United States Patent [19]

Chenciner et al.

[11] Patent Number: 5,112,748
[45] Date of Patent: May 12, 1992

[54] HYBRID CELLS PRODUCING AN ANTIGEN CHARACTERISTIC OF THE HEPATITIS B VIRUS OBTAINED FROM HEPATOCYTES AND ESTABLISHED MONKEY CELLS, A PROCESS FOR OBTAINING THESE HYBRID CELLS AND THEIR APPLICATION TO THE PRODUCTION OF THE AFORESAID ANTIGEN

[75] Inventors: Nicole Chenciner, Paris; Jean-Francois Houssais, Le Perray en Yvelines, both of France

[73] Assignee: Institut Pasteur and Centre National de la Recherche Scientifique, Paris, France

[21] Appl. No.: 31,465

[22] PCT Filed: Apr. 29, 1986

[86] PCT No.: PCT/FR86/00147

§ 371 Date: Feb. 19, 1987

§ 102(e) Date: Feb. 19, 1987

Related U.S. Application Data

[63] Continuation-in-part of Ser. No. 800,080, filed as PCT/FR86/00147, Apr. 29, 1989, abandoned.

[30] Foreign Application Priority Data

May 2, 1985 [FR] France .................. 85 06706

[51] Int. Cl.⁵ .............................. C12N 15/06
[52] U.S. Cl. .................. 435/172.2; 435/69.3; 435/70.2
[58] Field of Search ........... 435/240.26, 68, 172.2, 435/172.3, 948, 70.2, 69.3; 424/89; 530/806; 935/89, 92, 93, 95, 96, 107, 109

[56] References Cited

U.S. PATENT DOCUMENTS 4,608,339 8/1986 Yoakum et al. .......... 435/172.2

FOREIGN PATENT DOCUMENTS

| | | |
|---|---|---|
| 0022685 | 1/1981 | European Pat. Off. |
| 0062574 | 10/1982 | European Pat. Off. |
| 0093436 | 11/1983 | European Pat. Off. |
| 0145589 | 6/1985 | European Pat. Off. |
| 2487852 | 2/1982 | France . |
| WO82/03087 | 9/1982 | PCT Int'l Appl. |
| WO85/03946 | 9/1985 | PCT Int'l Appl. |
| 2010847 | 7/1979 | United Kingdom . |

OTHER PUBLICATIONS

Dubois et al., Proc. Natl. Acad. Sci., vol. 77, No. 8, pp. 4549-4553 (1980).
Houssais et al., C.R. Acad. Sci., vol. 297, pp. 497-500 (1983).
Kohler et al., Eur. J. Immunol., vol. 6, pp. 511-519 (1976).
Ochi et al., Proc. Natl. Acad. Sci., vol. 80, pp. 6351-6355 (1983).
Colbère-Garapin et al., "Late Transient Expression of Human Hepatitis B Virus Genes in Monkey Cells", EMBO J. 2(1): 21-25, 1983.
Carloni et al., "A Transformed Vero Cell Line Stably Producing the Hepatitis B Virus Surface Antigen", Gene 31: 49-57, 1984.

Primary Examiner—Robert A. Wax
Assistant Examiner—Keith C. Furman
Attorney, Agent, or Firm—Finnegan, Henderson, Farabow, Garrett & Dunner

[57] ABSTRACT

The invention concerns hybrid cells transformed or transformable by a cloned DNA containing the sequence coding for the antigen HBs. They are characterized in that they contain, on the one hand, at least a part of the genetic heritage of monkey hepatocyte cells and, on the other hand, a genetic marker permitting them to grow in a selective medium or one containing an active principle normally lethal to the VERO cells from which the hybrid is derived, but able to be inactivated by the polypeptide expressed by the said genetic marker.

9 Claims, No Drawings

HYBRID CELLS PRODUCING AN ANTIGEN CHARACTERISTIC OF THE HEPATITIS B VIRUS OBTAINED FROM HEPATOCYTES AND ESTABLISHED MONKEY CELLS, A PROCESS FOR OBTAINING THESE HYBRID CELLS AND THEIR APPLICATION TO THE PRODUCTION OF THE AFORESAID ANTIGEN

CROSS REFENCE TO RELATED APPLICATIONS

This application is a continuation-in-part of application Ser. No. 06/800,080, filed as PCT/FR86/00147, Apr. 29, 1989, now abandoned.

The invention relates to hybrid cells which are effective in the production of a polypeptide having the immunologic and, preferably also, immunogenic, properties of an antigen of the hepatitis B virus, preferably of an antigen of the envelope of this virus, more particularly of the antigen HBsAg or of a fragment of it, this polypeptide being coded by a cloned or clonable sequence of DNA in this cellular hybrid. The invention equally relates to a process for the production of these cellular hybrids and to their application to the production of the said polypeptide.

The cellular hybrids of the present invention enter into the context of those which have already been described in the parent application, Ser. No. 06/800,080. It will be recalled that the cellular hybrids of the main patent, which are transformed or transformable by a given cloned sequence of DNA, are characterized in that they contain, on the one hand, at least a part of the genetic heritage of a line of primary cells naturally favorable to the expression of natural genes coding for a protein constituted of the polypeptide coded by the aforesaid cloned DNA sequence or containing in its structure a polypeptide sequence identical or analogous to that of this polypeptide and, on the other hand, a genetic marker permitting them to grow in a selective medium or containing an active principle normally lethal to the cells from which the hybrid is derived, but able to be inactivated by the polypeptide expressed by the said genetic marker.

The expression "primary cells" as used in the preceding designates notably any cell taken from a mammal and known for its capacity to be the seat of production of the protein or polypeptide corresponding to this protein whose production is sought. These primary cells are characterized by the fact that they scarcely multiply in vitro, that their proliferation is at most limited to the production of monolayers, the development then being interrupted by "contact inhibition" or analog. This being so, these cells can, however, in any case, be maintained alive for a certain time in appropriate mediums.

The expression "established eukaryotic cells" refers to eukaryotic cells, more particularly mammalian cells which may be cultivated in vitro and which are capable of multiplying themselves over several generations.

The process according to the invention of the parent application, Ser. No. 06/800,080, for the formation of a cellular hybrid expressing or being rendered capable of expressing a given cloned sequence of DNA was characterized:

in that a co-culture is carried-out, under conditions appropriate to permit their hybridization, on the one hand, of the established eukaryotic cells, in which the aforesaid cloned DNA sequence is expressable or expressed and, on the other hand, of primary cells naturally favorable to the expression of natural genes coding for a protein constituted of a polypeptide coded by the aforesaid cloned DNA, or containing within its own structure a polypeptide sequence identical or analogous to that of this polypeptide, this co-culture being realized in a medium which does not permit the development of the said established cells, when they are not complemented by an appropriate genetic sequence, in that the primary cells used in the cellular hybridization are able or have previously been rendered able to provide the said appropriate genetic sequence to at least a part of the cell hybrids formed in the said culture medium and in that the cell hybrids formed are collected.

The invention of the parent application, Ser. No. 800,080 therefore provided modified micro-organisms transformed or transformable by cloned DNA sequences by using genetic engineering techniques, these modified micro-organisms however being such that the cloned DNA sequence in fact finds itself replaced in a genetic environment (intervening for example at the level of the differentiation or programation of the genomes containing an equivalent or identical DNA sequence) close to the natural conditions which in general prove particularly favorable to its expression.

The aim of the present invention is to provide a particularly preferred category of cellular hybrids, derived from monkey cells and monkey hepatocytes, for the production of an antigen of the hepatitis B virus, preferably HBsAg or a polypeptide presenting analogous immunogenic properties, these cellular hybrids being highly stable and capable of yields of antigen production heretofore rarely if ever achieved, in the micro-organisms transformed by genetic engineering techniques. In other words, the invention consists of the selection of particularly effective cellular hybrids among the categories of cellular hybrids defined in a more general fashion in the parent application, Ser. No. 800,080.

The cellular hybrids according to the invention, transformed or transformable by a cloned sequence of DNA containing all of a given gene contained in the genome of the hepatitis B virus, this sequence being incorporated or capable of being incorporated under conditions permitting its expression in the said cellular hybrid, is characterized in that it contains, on the one hand, at least a part of the genetic heritage of a line of monkey hepatocytes, preferably from chimpanzees or ververt monkeys, naturally favorable to the expression of natural genes contained in the genome of the hepatitis B virus and, on the other hand, a genetic marker permitting this cellular hybrid to grow in selective medium or one containing an active principle normally lethal to the monkey cells, but able to be inactivated by the polypeptide expressed by the said genetic marker. The cellular hybrid according to the invention preferably also contains at least a part of the genetic heritage of a line of established but non-tumoral nor oncogenic cells of monkey, preferably cells of the VERO line whose particular characteristics will be recalled further on.

The invention equally concerns a process for producing such a cellular hybrid in an appropriate culture medium, this process being characterized:

in that a co-culture is carried out, under conditions appropriate to allow their hybridization, on the one hand, of established non-tumoral monkey cells, in which the aforesaid part of the gene of the genome of the hepatitis B virus is expressable or expressed, these non-tumoral cells being however devoid of a given genetic sequence and, on the other hand, monkey hepatocytes, preferably from the chimpanzee, which are able or have first been rendered able to provide the said appropriate genetic sequence to at least a part of the cellular hybrids formed in the said culture medium and in that this co-culture is carried out in a medium which does not permit the development of the established monkey cells except when they are complemented by the said given or appropriate genetic sequence provided by the hepatocytes, and in that the hybrid cells formed are collected.

Any type of non-tumoral established monkey cell which may be maintained in culture may be used for the process according to the invention. Preferably recourse may be made to the heteroploid Vero cell lines of non-human primates, such as those described by PETRICIANI, J. C., KIRSCHENSTEIN, R. L., HINES, J. E., WALLACE, R.E. and MARTIN, D. P. ((1973) J. Natl. Cancer Inst., 51, 191–196). These latter cells have proved non-tumorigenic, even when tested on monkeys submitted to immuno-suppressive treatment.

The culture medium, as well as the established cells used, are chosen so as to satisfy the conditions described above. The medium and the established cells are such that the latter cannot develop in the chosen medium unless complemented by a genetic sequence, provided by the hepatocytes.

The established cells consist for example of cells presenting a natural or induced deficiency at the level of one of their genes, this deficiency preventing their development in the given medium, whereby this deficiency however may be compensated by the incorporation of a homologous gene expressable in the form of a protein homologous to that which would have been specified by the corresponding gene, if it had not been deficient. The cells having incorporated the homologous gene are then able to develop in the medium under consideration. It is to this possibility of compensation that the term "complementation" refers, which term was used in the most general definition of the process according to the invention, indicated above. Various examples of complementable genes or sequences of DNA have been mentioned for example in the French patent application No. 81.01137 filed the 2nd of Mar. 1981. To this type of DNA belong particularly those of the viruses called "Herpes simplex Virus" of type 1 (HSV1), the gene for thymidine kinase (TK), the gene for adenine phosphoribosyl-transferase (APRT) and for dihydrofolate reductase (DHFR), etc. for the enzyme xanthine-guanine phosphoribosyl-transferase (XGPRT), or of hypoxanthine guanine phosphoribosyl transferase (HGPRT).

To each of these "complementation DNAs" correspond mediums responding to the above-indicated conditions. In the preferred case of the present invention, in which one has recourse to VERO HGPRT³¹ cells, it is advantageous to use the medium known under the name of "HAT medium" (containing hypoxanthine and amino-pteridine in addition to thymidine). This medium is known not to permit the possible synthesis of thymidine phosphate except by the intermediary of the metabolic pathway called "salvation pathway", this pathway implying however that the integrity of the HGPRT gene of the cells likely to thus develop be preserved. Since the complementation nucleic sequence will be provided to them by the hepatocytes (themselves HGPRT⁻), only the hybrids to which the corresponding gene has been transmitted during the cellular fusion may develop in the chosen culture medium. The established cells not engaged in the constitution of a hybrid and not complemented cannot develop, just like the primary cells alone which, by their nature, have only a limited survival time.

In one equivalent mode of using the process according to the invention, recourse may be made to the introduction into the medium of a substance susceptible of preventing proliferation, or even to rapidly kill both types of cells, in the case where to that substance corresponds a second substance, notably an enzyme, which is capable of inactivating the former, the second substance being coded by a given DNA sequence susceptible of being first introduced into the primary cells. For example, the first substance may consist of an antibiotic such as that designated as G418, the second substance then consisting of an aminoglycoside 3'-phosphotransferase. Reference may also be made to the French patent application mentioned above No. 81.01137, for another illustration of this principle. As in the preceding case, only the hybrid having "inherited" from the primary cell the DNA sequence coding for the said aminoglycoside 3'-phosphotransferase, will survive.

According to a first alternative of the process according to the invention, either the established cells, or the hepatocytes, or both at once, have been transformed prior to the aforesaid co-culture by teh cloned DNA sequence containing a fragment of the genome of the hepatitis B virus.

The process according to the invention then includes a selection, after the aforesaid co-culture, of the aforesaid cellular hybrids formed, which prove also to be producers of the immunogenic peptide or of the antigen coded by the aforesaid cloned DNA sequence.

In a second alternative of the process according to the invention, it is the hybrid cells obtained, although non-secreting, which are transformed by the aforesaid DNA sequence, the process according to the invention then including again the selection, after the aforesaid co-culture of those of the cellular hybrids formed which prove also to be producers of the antigen, particularly of the HBsAg type coded by the given DNA sequence. In the preceding, the non-secreting hybrid may likewise be constituted of the hybrid obtained from primary cells and established cells which had not themselves first been transformed. Or they may have been, in which case the hybrid used for the transformation could be one of those not retained in the context of the selection of cellular hybrids considered in the first alternative.

The cloned sequence of DNA derived from the genome of the hepatitis B virus, whose expression is desired may consist of any natural gene fragment or any sequence resulting from a reverse transcription of a single-stranded nucleic acid, mRNA for example, by enzymatic means, or of any DNA obtained by chemical synthesis. For example, this sequence may consist of a cDNA coding for a polypeptide which is identical to that expressed by the corresponding-natural gene or an equivalent polypeptide, the equivalence resulting notably from the immunologic analogy susceptible of being recognized between these two polypeptides in the corresponding cross-reactions with antibodies previously formed between the natural polypeptide and the equivalent polypeptide. The expression "gene", as used above in the definition of the invention, should be interpreted as extending to any corresponding nucleotide sequence, such as mentioned above.

To achieve the transformation or transfection of the established cells or primary cells, before their hybridization, or of the hybrids already formed, recourse may be made to any vector, particularly an appropriate plasmid. The conditions this vector must satisfy are only those permitting the effective transformation and the expression of the cloned DNA sequence in the cells utilized. The specialist will be perfectly capable of choosing the types of plasmids to use, taking into account the nature of the cells to be used in the hybridization and possibly that of the DNA sequence to be cloned. When the sequence to be cloned is not already under the control of the promoter which will permit the expression of this sequence within the transformed cell, it will be advantageous to place it under the direct control of a promoter chosen from among those which permit not only the expression, but the excretion of the expressed polypeptide into the culture medium. Such promoters will be, for example, strong promoters such as those obtained from the viruses SV40 or MMTV.

Of course the vectors in question should still include all the genetic elements necessary to ensure the transcription and translation of the cloned DNA sequence in the monkey cell, for example the polyadenylation sites, and preferably also the ending of the transcription of the DNA sequence concerned. This being the case, it is not necessary to further specify the constitution of the plasmids susceptible of being used. A great number of these plasmids have been described in the technical literature. They may all be used once they are recognized to be capable of transforming mammalian cells, more particularly cells of the VERO line and to provide to the latter the gene or cloned DNA sequence susceptible of being transcribed and expressed in these cells.

Finally, the hybridization it itself of the established and primary cells may be accomplished under the classic conditions using, in a manner already known, any agent capable of weakening the cell walls to a point rendering fusion possible. One may classically use the Sendai virus or even more advantageously the polyalkylenepolyols (PEG 1000), notable polyethylene glycol, for example at a rate of 500 mg/ml or in solution at a rate of 40% weight/volume of culture medium without serum for 1 minute.

Other preferred characteristic of the invention will appear over the course of the description of the preferred embodiments of the process according the invention in the example which follows.

Strategy followed:
Use of monkey hepatocytes in primary culture, in fusion with normal monkey cells, VERO cells, which, in addition are HGPRT− (for subsequent selection) and which after integration of the S gene express it at a relatively low level.
selection of the hybrid clones, and study of their level of expression.

MATERIAL AND METHODS

1) Obtaining monkey cell lines producing the protein HBs, after transfection then selection of the producer clones VERO HGPRT− cells (monkey cells derived from VERO cells deficient in hypoxanthine guanine phosphoribosyl transferase, obtained by LEE, C. Y. et al (1983) have been co-transfected according to the technique described by GRAHAM, F. L. and VAN DER EB, A. J. ((1973), Virology 52, p. 456) by the DNA of two vectors, the one bearing the region coding for the protein HBs (plasmid pASV, sub-type ayw), the other (plasmid pW) carrying the gene for aminoglycoside-3'-phosphotransferase (APH 3'). The transfected cells expressing the enzyme APH 3' are selected in the presence of 400 microG/ml of aminoglycoside G418, according to the method of COLBERE-GARAPIN et al (1980). The clones resulting from this selection are then tested for the production of the HBs protein. $5.10^5$ VERO HGPRT− cells have been co-transfected by 10 g of DNA from the plasmid pASV and by 2 g of DNA from the plasmid pW. Four days after the transfection, the cells were divided in four and the selective medium was applied.

2) Origin of the transfected DNAs

The plasmid pASV is derived from the pAC2 plasmid (POURCEL et al 1982) and carries the gene coding for the S gene region of the HBV virus (Stu 43—BglII 1984 fragment), the replication origin of the SV 40 virus as well as the early promoter (PvuII 253-HindIII 5154 fragment). The pBR322 is deleted between 1120 and 2490 (R1 4360-SalI 650) (LUSKY M. et al 1981).

3) Obtaining, isolating and primary culturing of rat hepatocytes

The liver of a monkey (African green monkey) was obtained from the MERIEUX INSTITUTE.

The hepatocytes were isolated after perfusion of the liver with collagenase according to the method of SEGLEN (1973) with some modifications (GUGUEN-GUILLOUZO et al, 1980), HOUSSAIS, J. F. and CHENCINER, N. (1983).

The hepatocytes were cultured in Ham F12 medium, containing serum albumin, insulin and hydrocortisone, as well as 10% of fetal calf serum.

4) Fusion of VERO− (deposited Apr. 25, 1985 under the No. I-438) (expressing the S gene) with monkey cells in primary culture The fusion was carried out after the attachment of the hepatocytes to the plastic of the Falcon flasks, and their culture for 36 hours. $2.10^6$ cells of the different clones of the VERO HGPRT− cells (clone 3, clone 357) were added to the hepatocyte cultures, and after their attachment, the fusion was induced by a brief contact with polyethylene glycol (PEG), according to the methods described by DAVIDSON, R. L. and GERALD P. S. (1976); 24 hours later, these cultures were placed in the selective HAT medium (LITTLEFIELD, 1964) in order to eliminate the parental VERO HGPRT−. The unfused hepatocytes, fragilized by the PEG, were spontaneously eliminated.

In the weeks which followed, the viable hybrid clones were isolated, re-cultured and tested as to their capacity to produce the HBs antigen.

5) Detection and measurement of the production of HBs antigen in the culture medium The presence of the HBs antigen was detected using AUS-RIA II (Abbott) radio-immunological tests. The quantity of HBsAg excreted into the medium was determined relative to a standard curve established by dilution of standard HBsAg from ABBOTT.

RESULTS

Two cell lines (V3 and V357) obtained after transfection of the VERO HGPRT− cells were utilized for the fusion experiments with the monkey hepatocytes (HAS). The HBs antigen production levels for these two lines were the following:

V3 at 4th transfer: 36 ng/$10^6$ cells/24 hours (or 18 ng/$5.10^5$ cells)

V357 at 7th transfer: 65 ng/$10^6$/24 hours (or 32.5 ng/$5.10^5$ cells).

The HBs antigen production levels for the hybrid clones were distributed as follows:

| a) V357 > HAS hybrids (4 clones tested) |
|---|
| 190 ng/$5 \cdot 10^5$ cells/24 hours |
| 169 ng/$5 \cdot 10^5$ cells/24 hours |
| 95 ng/$5 \cdot 10^5$ cells/24 hours |
| 70 ng/$5 \cdot 10^5$ cells/24 hours |
| b) V3 > HAS hybrids |
| 484 ng/$5 \cdot 10^5$ cells/24 hours |
| 465 ng/$5 \cdot 10^5$ cells/24 hours |
| 384 ng/$5 \cdot 10^5$ cells/24 hours |
| 231 ng/$5 \cdot 10^5$ cells/24 hours |
| 714 ng/$5 \cdot 10^5$ cells/24 hours |
| 291 ng/$5 \cdot 10^5$ cells/24 hours |

In view of these results, it seems appropriate to note that:

the VERO cell alone, after integration of the S gene, has always, despite numerous efforts in various laboratories, expressed this gene only at a low level, in the V357×HAS hybrid, a coefficient of multiplication of from 2 to 5 times has been obtained, while in the V3 > HAS fusion, this coefficient is situated at between 12 and 40 times.

It will appear clearly to the specialist that the cellular hybrid system still presents a great latitude for optimization, for example in acting at the level of the vector and the transfected DNA sequences (cellular promoters, sequence enhancer ... )—and at the level of the hybrids (sub-clonings, isolation of the hyperproducing subclones ... ) or by modification of the composition of the culture medium, by addition of natural or synthetic molecules increasing the expression of the genes, etc.

In the preceding, the invention has been illustrated especially relative to the production of the HBs antigen. It is evident that the technique is applicable in the same fashion to the production of polypeptides coded by any other parts of the genome of the hepatitits B virus, for example to the production of the HBc antigen. Another preferred form addresses itself to cellular hybrids rendered producers (according to the same techniques as previously described) for the production of HBs particles bearing the peptide region called pre-S, containing a receptor for polymerized serum albumin.

The hybrid V3×HAS (b32e cells) has been deposited on Apr. 25, 1985 with the National Collection of Cultures of Micro-organisms (CNCM) of the Pasteur Institute of 25-28 rue du Docteur Roux, 75724 Paris Cedex 15, France under the No. I-438.

We claim:

1. A process for producing cellular hybrids which express a cloned DNA sequence of hepatitis B virus, comprising:

(A) co-transfecting non-tumoral monkey cells lacking a first selectable genetic marker with vector DNA encoding:

(1) a cloned DNA sequence of hepatitis B virus and
   (2) a second selectable genetic marker;

(B) selecting for transfected monkey cells, which express the second selectable genetic marker, in culture medium containing a substance that would be lethal to the transfected cell if the second selectable genetic marker was not present;

(C) testing said transfected monkey cells, which express the second selectable genetic marker, for expression of the cloned DNA sequence of hepatitis B virus;

(D) fusing in a co-culture said monkey cells lacking the first selectable genetic marker that express said cloned DNA sequence of hepatitis B virus with monkey hepatocytes containing the first selectable genetic marker to form cellular hybrids;

(E) selecting for viable cellular hybrids in selective culture medium; and (F) selecting for cells expressing said cloned DNA sequence of hepatitis B virus.

2. The process of claim 1, wherein said viable cellular hybrids are collected.

3. The process of claim 1, wherein the expression of said cloned DNA sequence of hepatitis B virus by said viable cellular hybrids is measured.

4. A process for producing cellular hybrids which express a cloned DNA sequence of hepatitis B virus, comprising:

(A) co-transfecting monkey hepatocytes lacking a first selectable genetic marker with vector DNA encoding:

(1) a cloned DNA sequence of hepatitis B virus and
   (2) a second selectable genetic marker;

(B) selecting for transfected monkey hepatocytes, which express the second selectable genetic marker, in culture medium containing a substance that would be lethal to the transfected cell if the second selectable genetic marker was not present;

(C) testing said transfected monkey hepatocytes, which express the second selectable genetic marker, for expression of the cloned DNA sequence of hepatitis B virus;

(D) fusing in a co-culture said monkey hepatocytes lacking the first selectable genetic marker that express said cloned DNA sequence of hepatitis B virus with non-tumoral monkey cells containing the first selectable genetic marker to form cellular hybrids;

(E) selecting for viable cellular hybrids in selective culture medium; and (F) selecting for cells expressing said cloned DNA sequence of hepatitis B virus.

5. The process of claim 4, wherein said viable cellular hybrids are collected.

6. The process of claim 4, wherein the expression of said cloned DNA sequence of hepatitis B virus by said viable cellular hybrids is measured.

7. A process for producing cellular hybrids which express a cloned DNA sequence of hepatitis B virus, comprising:

(A) providing non-tumoral monkey cells lacking a selectable genetic marker;

(B) providing monkey hepatocytes containing said selectable genetic marker;

(C) fusing in a co-culture said monkey cells and said monkey hepatocytes to form cellular hybrids;

(D) transfecting said cellular hybrids with a cloned DNA sequence of hepatitis B virus;

(E) selecting for viable cellular hybrids in selective culture medium; and (F) selecting for cells expressing said cloned DNA sequence of hepatitis B virus.

8. The process of claim 7, wherein said viable cellular hybrids are collected.

9. The process of claim 7, wherein the expression of said cloned DNA sequence of hepatitis B virus by said viable cellular hybrids is measured.

* * * * *

UNITED STATES PATENT AND TRADEMARK OFFICE
CERTIFICATE OF CORRECTION

PATENT NO. : 5,112,748

DATED : May 12, 1992

INVENTOR(S) : Chenciner et al.

It is certified that error appears in the above-identified patent and that said Letters Patent is hereby corrected as shown below:

Change the title, Col. 1, line 1 to read
--A METHOD OF PREPARING HYBRID CELLS PRODUCING AN ANTIGEN CHARACTERISTIC OF THE HEPATITIS B VIRUS--.

Signed and Sealed this

Seventh Day of December, 1993

Attest:

BRUCE LEHMAN

Attesting Officer

Commissioner of Patents and Trademarks